(12) United States Patent
Kawagishi et al.

(10) Patent No.: US 8,809,328 B2
(45) Date of Patent: Aug. 19, 2014

(54) IMIDAZOLE DERIVATIVE

(75) Inventors: Hirokazu Kawagishi, Shizuoka (JP); Jae-Hoon Choi, Shizuoka (JP)

(73) Assignee: National University Corporation Shizuoka University (JP)

( * ) Notice: Subject to any disclaimer, the term of this patent is extended or adjusted under 35 U.S.C. 154(b) by 0 days.

(21) Appl. No.: 14/113,730

(22) PCT Filed: Apr. 24, 2012

(86) PCT No.: PCT/JP2012/060989
§ 371 (c)(1),
(2), (4) Date: Dec. 19, 2013

(87) PCT Pub. No.: WO2012/147750
PCT Pub. Date: Nov. 1, 2012

(65) Prior Publication Data
US 2014/0148598 A1     May 29, 2014

(30) Foreign Application Priority Data

Apr. 27, 2011 (JP) .................. 2011-099456
Jul. 13, 2011 (JP) .................. 2011-154981
Feb. 28, 2012 (JP) .................. 2012-041711

(51) Int. Cl.
*A61K 31/535*    (2006.01)
*C07D 487/00*    (2006.01)

(52) U.S. Cl.
USPC .................... 514/230.5; 544/184

(58) Field of Classification Search
USPC ................... 544/184; 514/230.5
See application file for complete search history.

(56) References Cited

FOREIGN PATENT DOCUMENTS

| | | |
|---|---|---|
| JP | 63-068570 | 3/1988 |
| JP | 63-104965 | 5/1988 |
| JP | 04-210680 | 7/1992 |
| JP | 2009-001558 | 1/2009 |
| JP | 4565018 | 8/2010 |
| WO | WO 2011/010695 | 1/2011 |

OTHER PUBLICATIONS

PCT/IB/338 Notification of Transmittal of Copies of Translation of the International Preliminary Report on Patentability including PCT/IB/373 and PCT ISA/237 in counterpart WO Patent Application No. PCT/2012/060989)in English dated Nov. 28, 2013 (5 pages).
International Search Report mailed Jun. 12, 2012 in counterpart Application No. PCT/JP2012/060989.
Ivanovics, George A., et al., "The Synthesis of 2-substituted derivatives of 5-amino-1-.beta.-D-ribofuranosyl-imidazole-4-carboxamide. Ring opening reactions of 2-azapurine nucleosides", J. Org. Chem., vol. 39, 1974, p. 3651-p. 365-4.
Elliot Shaw et al. "Imidazo-1,2,3-Triazines As Substrates and Inhibitors for Xanthine Oxidase", J. Biol. Chem. vol. 194, 1952, p. 641-p. 654.

*Primary Examiner* — Jeffrey H Murray
*Assistant Examiner* — Oluwafemi Masha
(74) *Attorney, Agent, or Firm* — Ostrolenk Faber LLP

(57) ABSTRACT

An object of the present invention is to provide a compound that can regulate plant growth. The compound selected from the group consisting of (A) and (B):
(A) 3H-imidazo[4,5-d][1,2,3]triazin-4,6(5H,7H)-dione; and
(B) 3-methyl-3H-imidazo[4,5-d][1,2,3]triazin-4,6(5H,7H)-dione;
has a plant growth regulating action.

4 Claims, 8 Drawing Sheets

IMIDAZOLE DERIVATIVE

CROSS-REFERENCE TO RELATED APPLICATIONS

The present application is a 35 U.S.C. §§371 national phase conversion of PCT/JP2012/060989, filed Apr. 24, 2012, which claims priority to Japanese Patent Application Nos. 2011-099456, filed Apr. 27, 2011, 2011-154981, filed Jul. 13, 2011, and 2012-041711, filed Feb. 28, 2012, the contents of all of which are incorporated herein by reference. The PCT International Application was published in the Japanese language.

TECHNICAL FIELD

The present invention relates to an imidazole derivative.

BACKGROUND ART

As compounds to regulate plant growth, for example, phytohormones are known. Phytohormones are derived from plants themselves, but phytohormones also can be synthesized as compounds and are utilized as agricultural chemicals and vitalizing agents. As such compounds to regulate plant growth, imidazole derivatives are described in Patent Literatures 1 to 4. For example, in Patent Literature 4, 7H-imidazo[4,5-d][1,2,3]triazin-4(3H)-one (another name: 2-azahypoxanthine, hereinafter, sometimes referred to as "AHX") is described, and it is also described that AHX exhibits growth promotion or growth suppression action on plants.

CITATION LIST

Patent Literature

Patent Literature 1: Japanese Patent Application Laid-Open No. 63-104965
Patent Literature 2: Japanese Patent Application Laid-Open No. 63-68570
Patent Literature 3: Japanese Patent Application Laid-Open No. 4-210680
Patent Literature 4: Japanese Patent No. 4565018

SUMMARY OF INVENTION

Technical Problem

A compound, as AHX, that can regulate plant growth as well as can be used as an agricultural chemical or vitalizing agent for agriculture and gardening is required. Thus, an object of the present invention is to provide a novel compound that can regulate plant growth.

Solution to Problem

In the course of AHX study, the present inventors have found an AHX metabolite, 3H-imidazo[4,5-d][1,2,3]triazin-4,6(5H,7H)-dione (another name: 2-aza-8-oxohypoxanthine, hereinafter, sometimes referred to as "AOH"), that has a plant growth regulating action like AHX. Additionally, the inventors synthesized 3-methyl-3H-imidazo[4,5-d][1,2,3]triazin-4,6(5H,7H)-dione (hereinafter, sometimes referred to as "3-methyl-AOH") from AOH and have found that 3-methyl-AOH also has a plant growth regulating action. Therefore, the present invention provides a compound selected from the group consisting of the following (A) and (B):

(A) 3H-imidazo[4,5-d][1,2,3]triazin-4,6(5H,7H)-dione; and
(B) 3-methyl-3H-imidazo[4,5-d][1,2,3]triazin-4,6(5H,7H)-dione.

The present invention also provides a plant growth regulator comprising a compound selected from the group consisting of the above described (A) and (B). The compound of the present invention can be used effectively as a plant growth regulator because the compound can greatly promote plant growth.

The present invention also provides a method for producing AOH, comprising allowing xanthine oxidase to act on AHX to yield AOH. With this production method, it is possible to easily produce AOH at a high yield.

The present invention also provides a method for producing AOH comprising steps of: extracting a plant body to prepare an extract; and isolating AOH from the extract. With this production method, AOH can be yielded without resort to enzyme reaction.

Advantageous Effects of Invention

According to the present invention, a compound that can regulate plant growth is provided.

DESCRIPTION OF EMBODIMENTS

Figure 1:
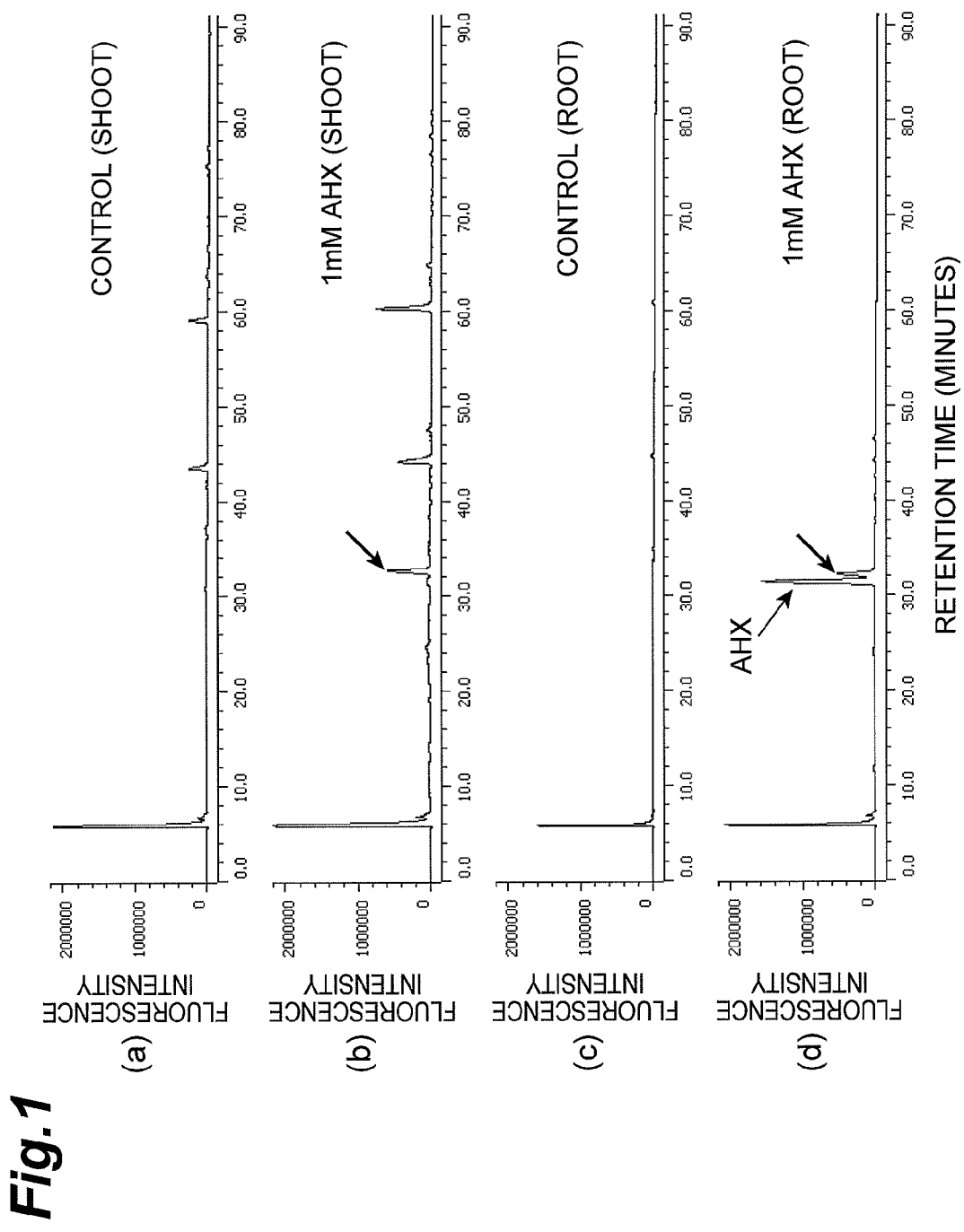
FIG. 1 is a chromatogram obtained from the chromatography of an extract of zoysiagrass cultivated in soil added with AHX.

The present invention provides (A) AOH, that is, 3H-imidazo[4,5-d][1,2,3]triazin-4,6(5H,7H)-dione. AOH is a compound represented by the following formula (I).

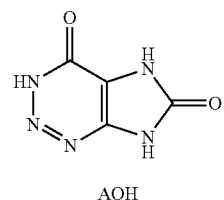

AOH

AOH can be obtained in accordance with the reaction of the following formula (II) by allowing xanthine oxidase to act on AHX, that is, 7H-imidazo[4,5-d][1,2,3]triazin-4(3H)-one.

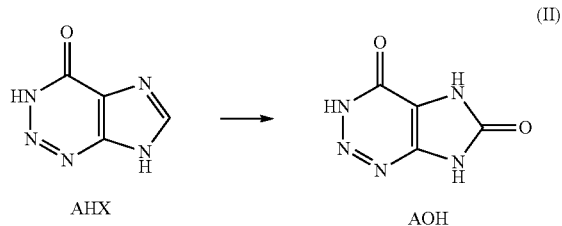

(II)

AHX AOH

Xanthine oxidase used for producing AOH from AHX is not particularly limited, and xanthine oxidase derived from, for example, butter milk can be used. To allow xanthine oxidase to act on AHX, for example, AHX is dissolved in a reaction solvent to make a reaction mixture, and xanthine oxidase may be added to the reaction mixture. The amount of xanthine oxidase to be added is, but not particularly limited to, preferably 20-200 U, more preferably 50-200 U, and more preferably 100-200 Upper 1 g of AHX. The reaction conditions are not particularly limited, and it is possible to allow xanthine oxidase to act, for example, within the range of its optimum reaction condition. For example, the reaction temperature is preferably 20 to 35° C., more preferably 25 to 32° C., and still more preferably 28 to 30° C. For example, the reaction time is preferably 6 to 50 hours, more preferably 24 to 50 hours, and still more preferably 48 to 50 hours. As the reaction solvent, although not particularly limited, water based solvents such as water or a buffer are preferred, and as the buffer, for example, phosphate buffer saline, phosphate buffer, and distilled water can be used. Additives such as a reaction activator may be added to the reaction mixture. It is possible to obtain AOH of the present invention from the reaction mixture by performing operations such as extraction, concentration, purification, and drying on the reaction mixture as appropriate after the completion of the reaction.

It is also possible to produce AOH from a plant body. The plants are not particularly limited as long as they produce AOH, and may be spermatophytes, pteridophytes, or bryophytes. The spermatophytes may be gymnosperms or angiosperms, and the angiosperms may monocotyledons or dicotyledons.

Such plants specifically include plants of the family Poaceae, the family Solanaceae, the family Theaceae, the family Compositae, the family Rosaceae, and the family Liliaceae. Among these, in the viewpoint that the production amount of AOH is large, plants of the family Poaceae or the family Solanaceae are preferable. The plants of the family Poaceae include the genus *Phyllostachys*, the genus *Hordeum*, the genus *Triticum*, the genus *Oryza*, the genus *Agrostis*, the genus *Zoysia*, the genus *Saccharum*, and the genus *Zea*. Among these, the genus *Oryza* is preferred, and rice (*Oryza sativa*) is more preferred. The plants of the family Solanaceae include the genus *Lycopersicon*, the genus *Solanum*, the genus *Capsicum*, the genus *Nicotiana*, the genus *Datura*, the genus *Physalis*, and the genus *Petunia*. Among these, the genus *Lycopersicon* is preferred, and tomato (*Solanum lycopersicum*) is more preferred.

Plants applied with AHX may be used as plants for producing AOH. When MIX is applied to plants, AOH is produced as an AHX metabolite. This AOH may be isolated from the plant body. If AHX is applied to plants, more AOH is produced from the plants than that usually produced by the plants.

As a method for producing AOH from a plant body, a method comprising steps of extracting a plant body to prepare an extract; and isolating AOH from the extract can be used. The method for preparing an extract by extracting a plant body includes, but not particularly limited to, for example, a method in which a plant organ of a plant body containing AOH are harvested, the plant organ is pulverized, and the pulverized organ is extracted with an organic solvent such as ethanol or acetone to prepare an extract. The method for isolating AOH from the extract is not particularly limited, but, for example, it is possible to isolate AOH of the present invention by performing operations such as concentration, purification, and drying on the obtained extract as appropriate.

The plant organ containing AOH may be, but not particularly limited to, an entire plant body, or any of roots, stems, leaves, flowers, reproductive organs, and seeds, and furthermore, may be culture cells. Among these, in the viewpoint of containing much AOH, roots are preferred.

The present invention also provides (B) 3-methyl-AOH, that is, 3-methyl-3H-imidazo[4,5-d][1,2,3]triazin-4,6(5H, 7H)-dione 3-methyl-AOH is a compound represented by the following formula (III).

(III)

3-methyl-AOH can be synthesized by methylating AOH, and 3-methyl-AOH can be synthesized in accordance with, for example, a method described in Examples.

With AOH or 3-methyl-AOH, it becomes possible to regulate plant growth. The plant growth in the present invention is not particularly limited as long as it is a phenomenon involving the usual differentiation or proliferation of plant cells, and includes not only expansion and enlargement of the organs constituting plant bodies but also germination from seeds, flower initiation, and seed formation. AOH and 3-methyl-AOH can promote or inhibit plant growth depending on type of plants to be targeted, the concentration of AOH or 3-methyl-AOH, and the part of plants to be made contact with AOH or 3-methyl-AOH. Thus, it is possible to use a plant growth regulator comprising AOH or 3-methyl-AOH as a growth promoter or a growth inhibitor for various organs of plants depending on target plants and purposes.

The plants to be targeted are not particularly limited, as long as they are plants subjected to a growth regulating action by AOH or 3-methyl-AOH. The plants to be targeted may be spermatophytes, pteridophytes, or bryophytes, the spermatophytes may be gymnosperms or angiosperms, and the angiosperms may monocotyledons or dicotyledons.

Such plants specifically include plants of the family Poaceae, the family Solanaceae, the family Theaceae, the family Compositae, the family Rosaceae, and the family Liliaceae. Among these, in the viewpoint that the growth regulating action by AOH is significant, it is preferable to be plants of the family Poaceae. The plants of the family Poaceae include the genus *Phyllostachys*, the genus *Hordeum*, the genus *Triticum*, the genus *Oryza*, the genus *Agrostis*, the genus *Zoysia*, the genus *Saccharum*, and the genus *Zea*. Among these, the genus *Oryza* or the genus *Zoysia* is preferred.

The plant organ to be targeted may be, but not particularly limited to, any of roots, stems, leaves, flowers, reproductive organs, and seeds, and furthermore, may be culture cells. Among these, in the viewpoint that the growth regulating action by AOH is significant, it is preferable to be roots, stems, leaves, or seeds.

The concentration and the contact method of AOH or 3-methyl-AOH to be applied on plants can be selected as appropriate depending on type of plants to be targeted, their organs, purposes, and the like. For example, in a case that the target plant is rice (*Oryza sativa*), the target organ is the stem, and the purpose is to extend the length of the stem, it is preferable to cultivate the plant with a culture fluid in which AOH is dissolved to become 5 to 2000 μM in a normal culture fluid. In this case, the concentration of AOH in the culture fluid is more preferably 100 to 1500 μM, and yet more preferably 500 to 1000 μM. In a case that the target plant is *Oryza sativa*, the target organ is the root, and the purpose is to extend the length of the root, it is preferable to cultivate the plant with a culture fluid in which AOH is dissolved to become 50 to 2000 μM in a normal culture fluid. In this case, the concentration of AOH in the culture fluid is more preferably 250 to 1500 μM, and yet more preferably 500 to 1000 μM. In a case that the target plant is *Oryza sativa*, the target organ is seeds, and the purpose is to increase the size or number of seeds to increase the yield of seeds, it is preferable to cultivate the plant with a culture fluid in which AOH is dissolved to become 5 to 1000 μM in a normal culture fluid. Alternatively, in the case that the purpose is to increase the yield of the seed of *Oryza sativa*, it is also preferable to cultivate *Oryza sativa* in soil with applying a culture fluid in which AOH is dissolved to become 5 to 500 μM.

For 3-methyl-AOH, for example, in a case that the target plant is *Oryza sativa*, the target organ is the root, and the purpose is to extend the length of the root, it is preferable to cultivate the plant with a culture fluid in which 3-methyl-AOH is dissolved to become 50 to 1000 μM in a normal culture fluid. In this case, the concentration of 3-methyl-AOH in the culture fluid is more preferably 200 to 500 μM.

The plant growth regulator comprising AOH or 3-methyl-AOH of the present invention may contain bactericides, anti-mold agents, insecticides, or compounds having a plant growth regulating action other than AOH or 3-methyl-AOH, in addition to AOH or 3-methyl-AOH. Furthermore, the regulator may contain known additives for formulation. As such additives for formulation, it is possible to use, but not particularly limited to, for example, excipients, emulsifiers, and humectants. The types of the form of the plant growth regulator of the present invention can be, but not particularly limited to, for example, emulsions, wettable powders, water soluble powders, solutions, granules, powders, microcapsules, fumigants, smoking agents, aerosols, flowable agents, pastes, tablets, coating agents, ultra-low-volume spraying agents, oil agents, and complex fertilizers, and users can select as appropriate depending on type of plants to be targeted, their organs, purposes, and the like. Plant growth regulator in these forms can be produced with known methods.

EXAMPLES

Hereinbelow, the present invention is described more specifically in reference to Examples, but the present invention is not intended to be limited to these Examples.

Example 1

Detection of an AHX Metabolite of Zoysiagrass

Zoysiagrass (*Agrostis stolonifera*) was cultivated in a control section of a normal agar medium (100 mL) and in an AHX section of an agar medium added with 1 mM AHX (100 mL) for 30 days. Extension of shoots of the zoysiagrass in the MIX section was clearly promoted compared to that of the zoysiagrass in the control section. The shoots and roots of the cultivated zoysiagrass were harvested, extracted with ethanol, and the extract of shoots and the extract of the roots were subjected to reversed-phase high performance liquid chromatography (reversed-phase HPLC). The analysis conditions were as follows. Column: Develosil C30-UG-5 column (size 4.6×250 mm), flow rate: 0.5 mL/minute, mobile phase: gradient elution of 2% methanol in 0.05% trifluoroacetic acid (liquid A) for 12 minutes; 2-100% methanol in the liquid A for 120 minutes; 100% methanol for 20 minutes, detection: absorbance measurement at UV 254 nm. A chromatogram obtained with chromatography is shown in FIG. 1. No peak of AHX was detected but a peak of AHX metabolite was detected from the eluate of the shoot extract of the AHX section (FIG. 1 (*b*)). Peaks of AHX and the AHX metabolite were detected from the eluate of the root extract of the AHX section (FIG. 1(*d*)). It is believed that this is because, other than the AHX metabolite in the roots, the AHX in the medium is contaminated into the eluate of the root extract. Neither a peak of AHX nor a peak of the AHX metabolite was detected from the eluates of the shoot extract and the root extract of the control section (FIGS. 1(*a*) and (*c*)).

Example 2

Detection of an AHX Metabolite of Rice

Figure 2:
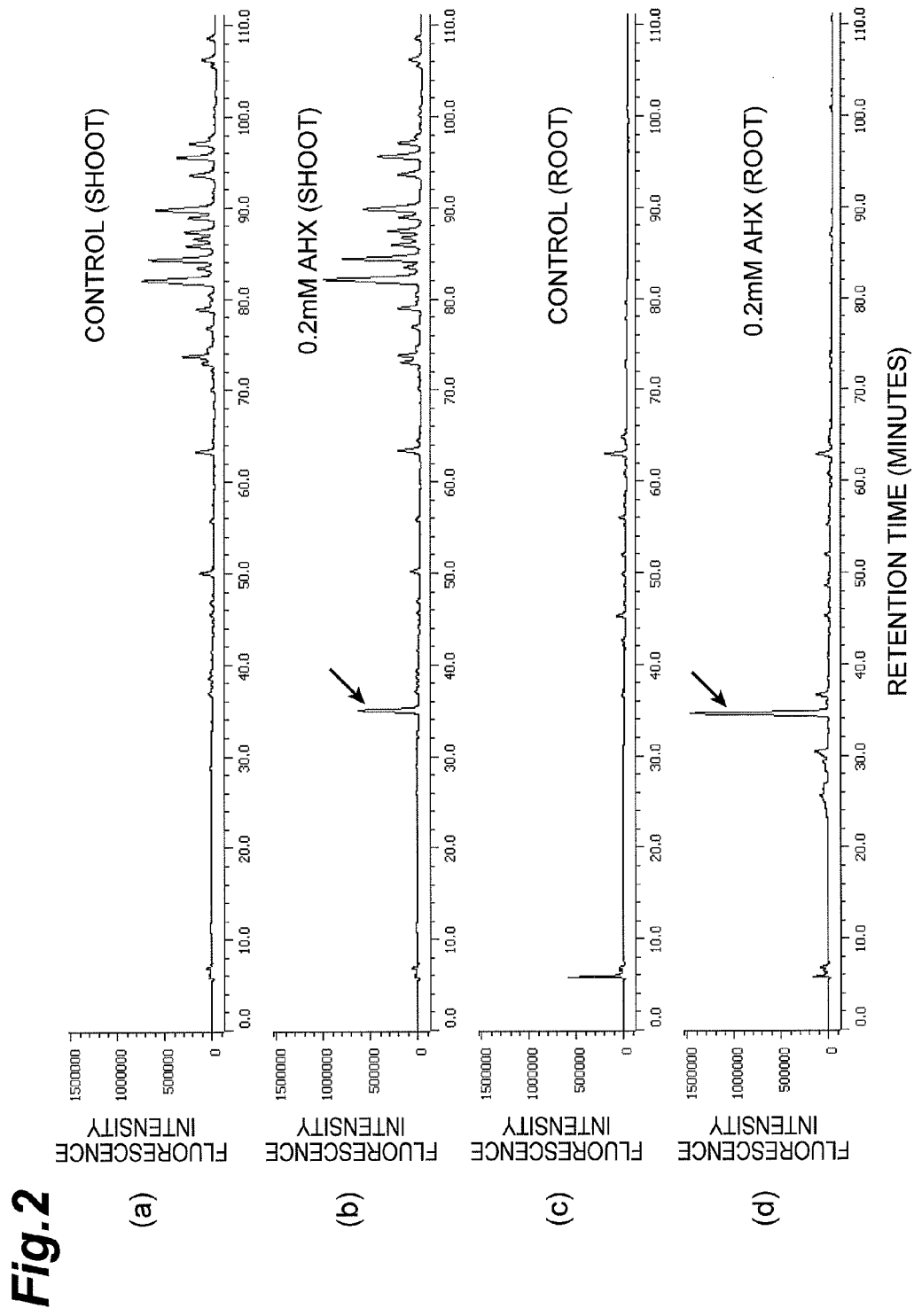
FIG. 2 is a chromatogram obtained from the chromatography of an extract of rice cultivated in a culture fluid added with AHX.

Rice (*Oryza sativa*) was cultivated in a control section of a normal culture fluid and in an MIX section of a culture fluid in which AHX was added to be 0.2 mM in the normal culture fluid for 14 days. Extension of shoots of the rice in the AHX section was clearly promoted compared to that of the rice in the control section. The shoots and roots of the cultivated rice were harvested, extracted and analyzed with reversed-phase HPLC as in Example 1. A chromatogram obtained with chromatography is shown in FIG. 2. In the MIX section, no peak of AHX was detected neither from the eluate of the shoot extract nor from the eluate of the root extract, but a peak of the AHX metabolite was detected (FIGS. 2(*b*) and (*d*)). Neither a peak of AHX nor a peak of the AHX metabolite was detected from the eluates of the shoot extract and the root extract of the control section (FIGS. 2(*a*) and (*c*)).

Example 3

Isolation of the AHX Metabolite

Rice (*Oryza sativa*) was cultivated in a control section of a normal culture fluid and in an AHX section of a culture fluid in which AHX was added to be 1 mM in the normal culture fluid for 20 days. Shoots (360 g) of the cultivated rice were harvested and extracted with ethanol. An ethanol-soluble fraction was concentrated under reduced pressure and extracted with dichloromethane. A dichloromethane-insoluble fraction was extracted with ethanol to yield an ethanol-soluble fraction (9.8 g). The ethanol-soluble fraction was subjected to silica gel chromatography (filler: 350 g of silica gel 60N, column size: 4×60 cm) and eluted sequentially with mixtures of dichloromethane: methanol=9:1, 7:3, 5:5 to yield eight fractions. Among these, the fraction 3 (288 mg) was purified sequentially with HPLC (column: Develosil C30-UG-15/30 column, size: 50×500 mm, flow rate: 25 mL/min, mobile phase: 5% methanol, detection: UV 310 nm) and HPLC (column: Develosil C30-UG-5 column, size: 20×250 mm, flow rate: 5 mL/minute, mobile phase: 10% methanol, detection: UV 310 nm) to finally isolate 10.5 mg of an AHX metabolite.

Example 4

Determination of the Structure with X-Ray Crystal Structure Analysis

Figure 3:
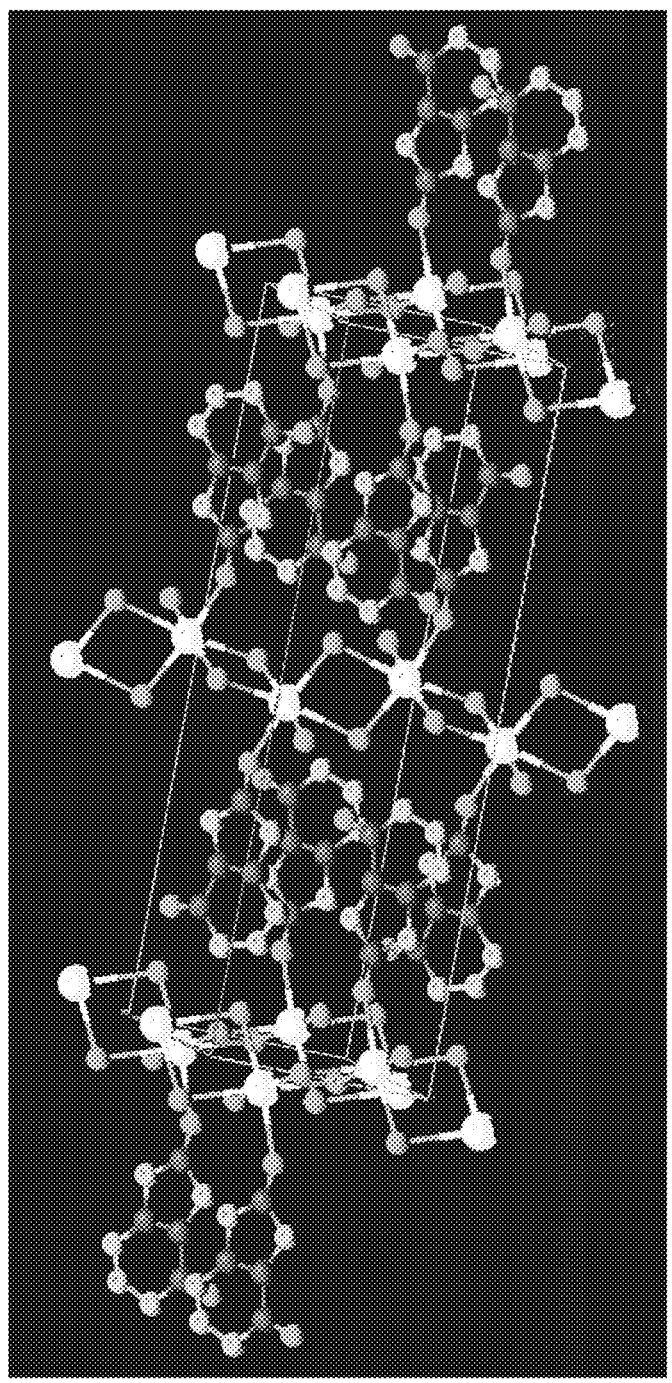
FIG. 3 is a diagram showing the crystal structure of an AHX metabolite determined with X-ray crystal structure analysis.

X-ray crystal structure analysis was performed on the isolated AHX metabolite as follows. Single-crystal X-ray diffraction measurement was performed using SPring-8 (single crystal structure analysis beamline BL02B1). The measurement conditions were as follows. Wavelength: 0.8260 (4) Å, beam size: length 140×width 159 µm$^2$, Photon Flux: 1.81× 10$^8$ photons/sec, and Photon Flux Density: 8.13×10$^3$ photons/sec/µm$^2$. FIG. 3 is a diagram showing the crystal structure of the AHX metabolite obtained with X-ray crystallography. From X-ray crystallography, it was confirmed that the isolated AHX metabolite was 3H-imidazo[4,5-d][1,2,3]triazin-4,6(5H,7H)-dione (another name: 2-aza-8-oxohypoxanthine, "AOH") having the structure of formula (I).

Example 5

Production of AOH

AOH was produced by allowing xanthine oxidase to act on AHX as follows. In 1 L of phosphate buffer saline (10 mM, pH 7.4), 137 mg of AHX was dissolved thereto, 25 mg of xanthine oxidase (derived from butter milk, 0.28 U/mg) was added, and the resultant mixture was left to stand at 30° C. To the mixture, 25 mg of the xanthine oxidase was added three times every 24 hours. After the last addition, the mixture was left to stand for further 24 hours. That is, in the total amount, 100 mg of xanthine oxidase was allowed to act on 137 mg of AHX for 96 hours. Consequently, it was confirmed with analysis of HPLC (Develosil C30-UG-5 column (size 4.6× 250 mm), flow rate: 0.5 mL/minute, mobile phase: gradient elution of 2% methanol in 0.05% trifluoroacetic acid (liquid A) for 12 minutes; 2-100% methanol in the liquid A for 120 minutes; 100% methanol for 120 minutes; detection: absorbance at UV 254 nm) that AHX was completely converted to AOH. The product was purified with ODS gel flash chromatography (filler: 350 g of ODSgel, column size: 4×60 cm, mobile phase: water, water/methanol=9:1) to isolate 120 mg of AOH (yield 78.4%). It was confirmed by the HPLC retention time, the absorbance wavelength, and mass spectrometry that the isolated substance was AOH.

Example 6

The Influence of AOH on Rice

Figure 4:
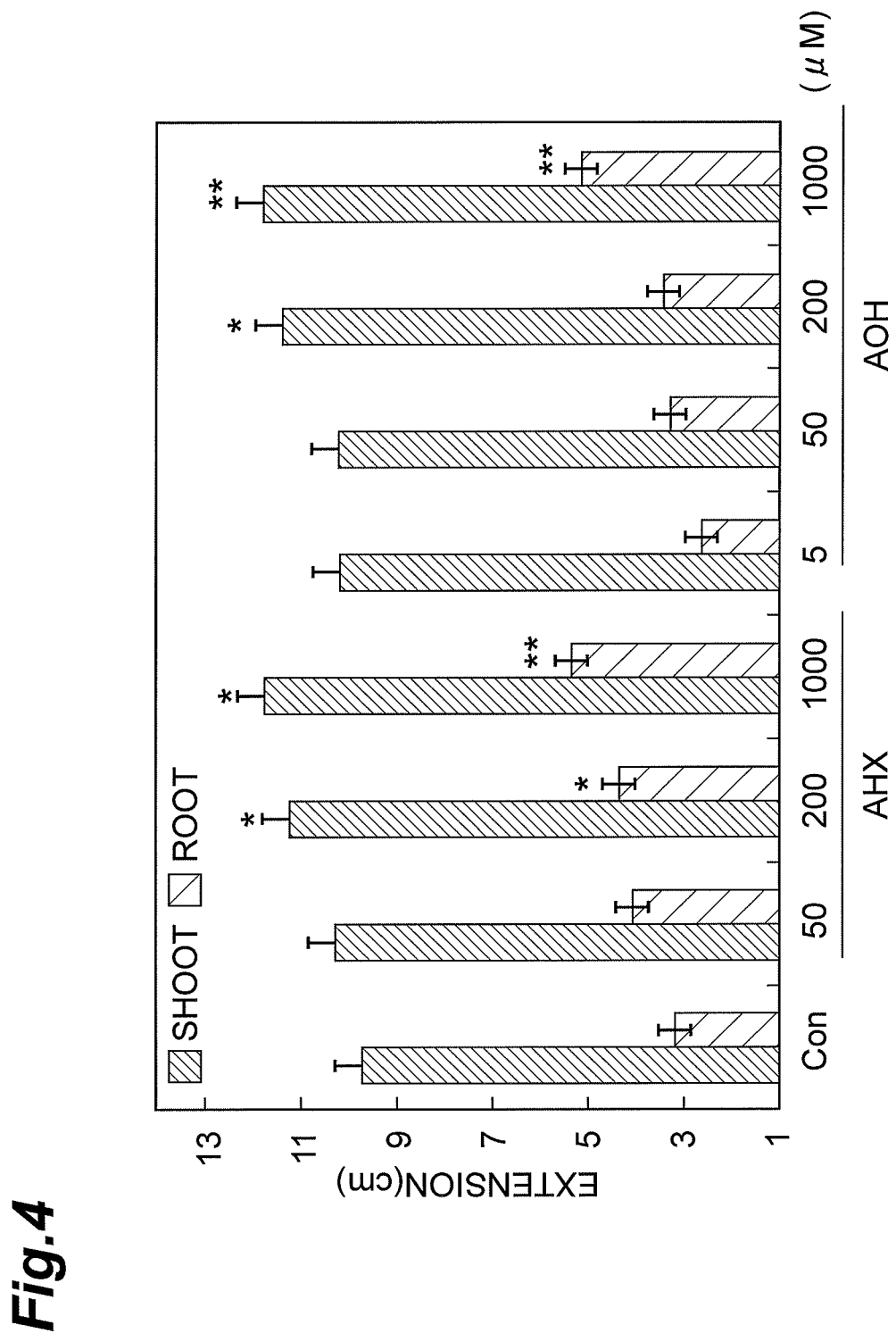
FIG. 4 is a graph showing the influence of addition of AHX or AOH to a medium on rice growth.

Sterilized seeds of rice (Nipponbare) (*Oryza sativa* L. cv. Nipponbare) were allowed to sprout at 28° C. in three days. The sprouted seeds (four seeds per test tube) were cultivated in a test tube, in which a control culture fluid or a culture fluid to which AHX or AOH was added to different concentrations and was placed, at 28° C. for a week. AOH that was produced according to the method of Example 5 was used. The control culture fluid comprises 0.5 mM of $NH_4NO_3$, 0.3 mM of $Na_2HPO_4$, 0.15 mM of $K_2SO_4$, 0.2 mM of $MgCl_2$, 0.1 mM of $CaCl_2$, 23 µM of Fe-ethylenediaminetetraacetic acid (Fe-EDTA), 25 µM of $H_3BO_3$, 4.5 µM of $MnSO_4$, 0.15 µM of $CuSO_4$, 0.35 µM of $ZnSO_4$, and 0.05 µM of $Na_2MoO_4$. As for the culture fluids containing AHX or AOH, AHX or AOH is added to the above described control culture fluids such that the final concentration becomes 50 µM, 200 µM or 1000 µM. The culture fluid was replaced with new culture fluid every other day. After cultivation, the length of shoots and roots was measured. The measured extension of the shoots and roots is shown in FIG. 4. It was confirmed that AOH, similarly to AHX, promoted extension of shoots and roots concentration-dependently and that AOH was an Ala metabolite (in FIG. 4, "Con" represents control. "*" indicates the P value <0.05 and "**" indicates the P value <0.01. n=11.).

Example 7

Isolation of AOH from Rice

Figure 5:
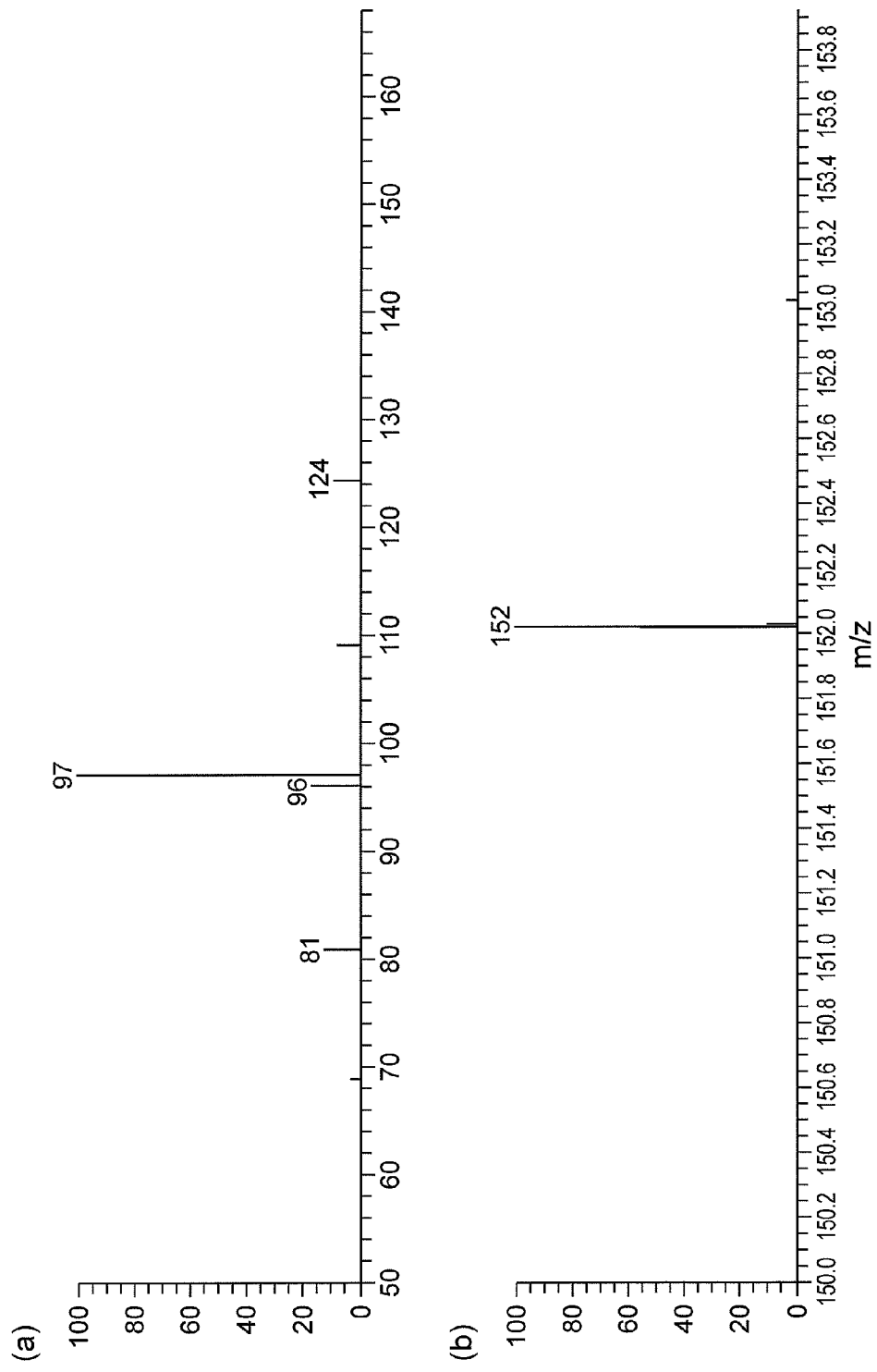
FIG. 5 is (a) an MS/MS spectrum and (b) a full mass spectrum of a standard AOH.
Figure 6:
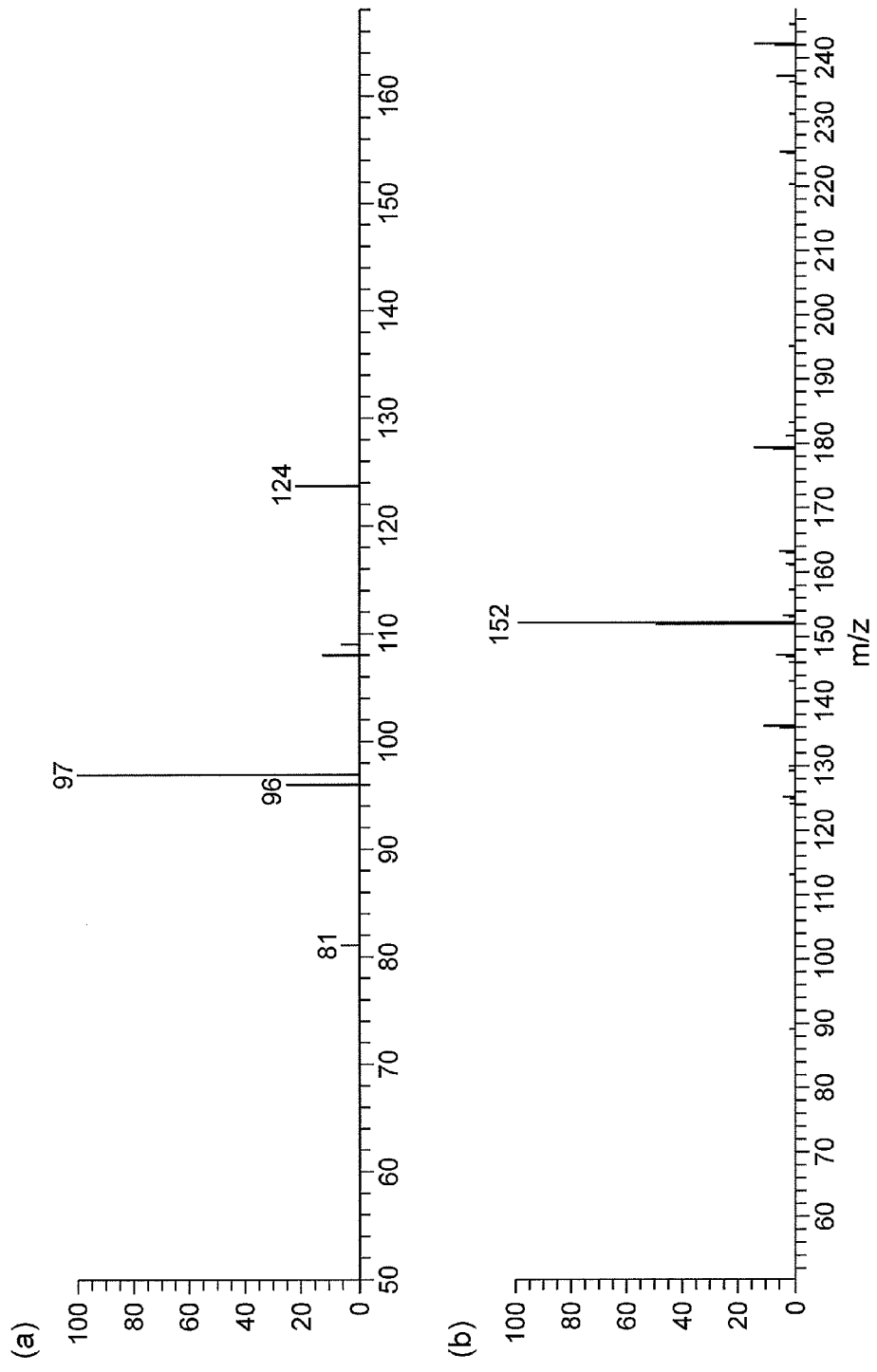
FIG. 6 is (a) an MS/MS spectrum and (b) a full mass spectrum of a rice root extract.

Rice (*Oryza sativa*) was hydroponically cultivated with a normal culture fluid for rice for two months, and roots (52 g) were harvested. After the roots were pulverized with a mixer, the pulverized roots were extracted with ethanol and acetone, and the extract was then concentrated to dryness thereby to obtain root extract (340 mg). This extract was dissolved in a solvent (95% acetonitrile and 0.05% formic acid) to adjust to a concentration of 10 mg/mL, and the resultant solution was analyzed with a liquid chromatography-tandem mass spectrometer (LC-MS/MS). The reference standard AOH has a peak at a retention time of 3.5 minutes with LC, a peak of a molecular weight of 152.0[M−H]− was detected from a full mass spectrum at this retention time, and a peak of a fragment ion of molecular weight of 97 was detected from an MS/MS spectrum. Similarly to the reference standard AOH, the rice root extract has a peak at a retention time of 3.5 minutes with LC, a peak of a molecular weight of 152.0[M−H]− was detected from a full mass spectrum at this retention time, and a peak of fragment ion of a molecular weight of 97 was detected from an MS/MS spectrum. Since the same molecular weight peak as that of the reference standard AOH was detected from the extract of the rice, it was confirmed that the rice roots contained endogenous AOH. The MS/MS spectrum (a) and the full mass spectrum (b) of the reference standard AOH are shown in FIG. 5. The MS/MS spectrum (a) and the full mass spectrum (b) of the rice root extract are also shown in FIG. 6. The amount of AOH contained in the rice roots, which was calculated on the basis of the calibration curve and the peak area of AOH, was about 2.5 ng per 52 g of the rice roots. The LC-MS/MS analysis conditions and the apparatuses used are as follows.

<The LC-MS/MS Analysis Conditions and the Apparatus>
(LC part)
Pump: LC-20AD (SHIMADZU CORPORATION)
Column: PC HILIC (size: 2.0 mm×100 mm, Shiseido Co., Ltd.)
Flow rate: 0.2 mL/minute
Injection amount: 10 µL
(MS/MS part)
Mass spectrometer: LTQ ORBITRAP DISCOVERY (Ion trap type, Negative mode, THERMO SCIENTIFIC)

Example 8

Isolation of AOH from Tomato

Figure 7:
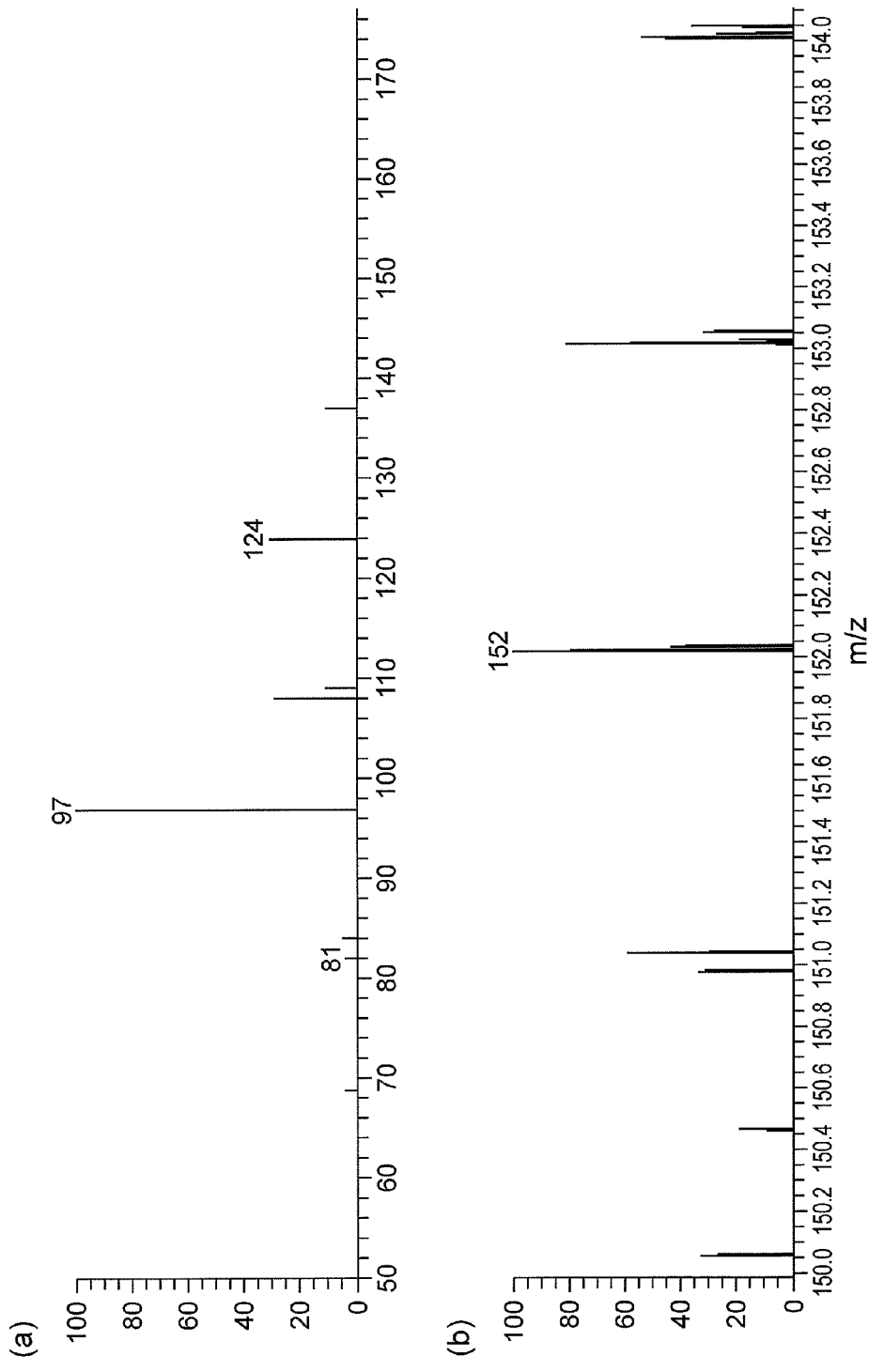
FIG. 7 is (a) an MS/MS spectrum and (b) a full mass spectrum of a tomato root extract.

Tomato (*Solanum lycopersicum*) was hydroponically cultivated with a normal culture fluid for tomatoes for two months, and roots (17 g) were harvested. After the roots were pulverized with a mixer, the pulverized roots were extracted with ethanol and acetone, the extract was then concentrated to dryness, and were stripped of the dichloromethane-soluble part to obtain root extract (4.7 mg). This extract was dissolved in a solvent (95% acetonitrile, 0.05% formic acid) to adjust to a concentration of 10 mg/mL, and the resultant solution was analyzed with an LC-MS/MS as in Example 7. The analysis conditions and apparatuses used for analysis were the same as in Example 7. Consequently, the tomato root extract, similarly to the reference standard AOH, has a peak at retention time 3.5 minutes with LC, a peak of molecular weight 152.0 [M−H]− was detected from a full mass spectrum at this retention time, and a peak of fragment ion of molecular weight 97 was detected from an MS/MS spectrum. Thus, it was confirmed that the tomato roots also contained endogenous AOH. The MS/MS spectrum (a) and the full mass spectrum (b) of the tomato root extract are shown in FIG. 7. The amount of AOH contained in the tomato roots, which was calculated on the basis of the calibration curve and the peak area of AOH, was about 0.1 ng or less per 17 g of the tomato roots, which was lower than that in the rice.

Example 9

The Influence of AOH on Soil Cultivation of Rice (Pot Cultivation)

Rice (Nipponbare) (*Oryza sativa* L. cv. Nipponbare) was sown on Apr. 29, 2011, and each of grown seedlings was transplanted to a pot (1/5000a pot) filled with soil which contains a fertilizer comprising N (1440 mg), $P_2O_5$ (12 mg), $K_2O$ (760 mg) and CaO (806 mg) on June 7th, and was soil-cultivated in a greenhouse (28° C.) under any one of seven types of cultivation conditions of the following (1) to (7) until September 24th. Supply of water was performed by providing two liter of tap water or tap water to which AOH was added every week (see below).

Cultivation Conditions
(1) Tap water was provided during pot cultivation.
(2) Tap water to which AOH was added such that the final concentration became 50 μM was provided for two weeks (from June 7th to June 20th) in the planting stage. Tap water was provided in the other period.
(3) Tap water to which AOH was added such that the final concentration became 50 μM was provided for two weeks (from July 4th to July 17th) in the tillering stage. Tap water was provided in the other period.
(4) Tap water added to which AOH was added such that the final concentration became 50 μM was provided for two weeks (from July 25th to August 7th) in the topdressing stage for panicle formation. Tap water was provided in the other period.
(5) Tap water added to which AOH was added such that the final concentration became 50 μM was provided for two weeks (from August 15th to August 28th) in the topdressing stage for ripening. Tap water was provided in the other period.
(6) Tap water to which AOH was added such that the final concentration became 4 μM was provided during pot cultivation.
(7) Tap water to which AOH was added such that the final concentration became 50 μM was provided during pot cultivation.

Brown rice and plant bodies soil-cultivated were dried at 30° C. for 15 days, and brown rice weight (both of weight per plant and weight per 100 brown rice grains), panicle length, culm length, number of panicles, number of tillers, and aerial part weight were measured. The results are shown in Table 1. By applying AOH all the time, the number of panicles and the aerial part weight were increased more than the control. Additionally, by applying AOH in the topdressing stage for panicle formation stage or later, the brown rice weight per plant was increased more than the control (In Table 1, numerical values indicate the average±standard deviation. "Increasing rate" indicates an increasing rate (%) relative to the control. "*" indicates the P value <0.05. Number of samples (pots)=6.).

TABLE 1

|  | Control | 50 μM AOH Planting stage | 50 μM AOH Tillering stage | 50 μM AOH Topdressing stage for panicle formation |
|---|---|---|---|---|
| Brown rice |  |  |  |  |
| Brown rice weight (g/plant) | 41.7 ± 10.9 | 46.6 ± 9.43 | 42.3 ± 12.2 | 53.7 ± 3.59* |
| Increasing rate (%) |  | 12 |  | 29 |
| Brown rice weight (g/100 grains) | 2.19 ± 0.06 | 2.11 ± 0.07 | 2.12 ± 0.12 | 2.12 ± 0.07 |
| Plant body |  |  |  |  |
| Number of tillers | 31.3 ± 3.30 | 34.6 ± 2.70 | 30.9 ± 3.67 | 31.6 ± 3.60 |
| Panicle length (cm) | 25.3 ± 1.91 | 23.5 ± 1.61 | 26.2 ± 1.03 | 24.5 ± 1.61 |
| Culm length (cm) | 95.3 ± 7.45 | 97.1 ± 12.1 | 94.5 ± 4.63 | 90.2 ± 6.15 |
| number of panicles | 26.5 ± 4.76 | 27.8 ± 4.26 | 23.0 ± 5.44 | 30.5 ± 4.50 |
| Increasing rate (%) |  |  |  |  |
| Aerial part (g) | 116 ± 23.8 | 125 ± 21.2 | 112 ± 30.0 | 134 ± 16.5 |
| Increasing rate (%) |  |  |  |  |

|  | 50 μM AOH Topdressing stage for ripening | 5 μM AOH All the time | 50 μM AOH All the time |
|---|---|---|---|
| Brown rice |  |  |  |
| Brown rice weight (g/plant) | 53.2 ± 2.61* | 59.3 ± 2.27* | 58.2 ± 3.76* |

TABLE 1-continued

| | | | |
|---|---|---|---|
| Increasing rate (%) | 28 | 42 | 40 |
| Brown rice weight (g/100 grains) | 2.18 ± 0.08 | 2.13 ± 0.09 | 2.15 ± 0.16 |
| Plant body | | | |
| Number of tillers | 31.4 ± 3.91 | 37.9 ± 3.71* | 35.7 ± 4.15* |
| Panicle length (cm) | 24.0 ± 2.07 | 24.5 ± 2.24 | 24.4 ± 1.96 |
| Culm length (cm) | 92.8 ± 3.98 | 89.7 ± 6.40 | 92.3 ± 5.64 |
| number of panicles | 28.8 ± 4.67 | 32.8 ± 2.48* | 32.7 ± 4.03* |
| Increasing rate (%) | | 24 | 23 |
| Aerial part (g) | 131 ± 13.3 | 151 ± 6.19* | 147 ± 9.63* |
| Increasing rate (%) | | 30 | 27 |

Example 10

The Influence of AOH on Soil Cultivation of Rice (Field Cultivation)

Rice (Nipponbare) (*Oryza sativa* L. cv. Nipponbare) was used and cultivated in a field as follows. As cultivation conditions, five sections of (1) to (5) were set.

Rice (Nipponbare) (*Oryza sativa* L. cv. Nipponbare) was sown in a nursery box on Apr. 29, 2011, and provided with a total of 15 liters of tap water or tap water to which AOH was added for two weeks from May 24th while raising seedling in the nursery box. On June 7th, each of grown seedlings was transplanted to the field. The planting density was set to the interrow space of 30 cm and the planting distance of 15 cm (three reproductions of 3×3.3 m per one section). As basal fertilizer, 50 L of tap water or tap water to which AOH was added per section was supplied on June 7th. The cultivation was continued, and as topdressing for panicle formation, 50 L of tap water or tap water to which AOH was added per section was supplied on July 25th. Plant bodies were harvested on October 12th.

Cultivation Conditions (1) Tap water was used as the culture fluid during seedling raising, the basal fertilizer, and the topdressing for panicle formation.

(2) Tap water to which AOH was added such that the final concentration became 0.5 mM was provided as the culture fluid during seedling raising. Tap water was used as the basal fertilizer, and the topdressing for panicle formation.

(3) Tap water to which AOH was added such that the final concentration became 1.0 mM was provided as the culture fluid during seedling raising. Tap water was used as the basal fertilizer and the topdressing for panicle formation.

(4) Tap water to which AOH was added such that the final concentration became 0.5 mM was provided as the basal fertilizer. Tap water was used as the culture fluid during seedling raising and the topdressing for panicle formation.

(5) Tap water to which AOH was added such that the final concentration became 0.5 mM was provided as the topdressing for panicle formation. Tap water was used as the culture fluid during seedling raising and the basal fertilizer.

Brown rice was dried, and total brown rice weight, hull weight, non-sieved brown rice weight and sieved brown rice, per 10 plant bodies, and thousand kernel weight were measured. The results are shown in Table 2. By applying AOH, the total brown rice weight, the hull weight, the non-sieved brown rice weight, and the sieved brown rice were increased more than the control (In Table 2, numerical values indicate the average±standard deviation. "Increasing rate" indicates an increasing rate (%) relative to the control. "*" indicates the P value <0.05.).

TABLE 2

| Per 10 plants | Control | 0.5 mM AOH During seedling raising | 1.0 mM AOH During seedling raising |
|---|---|---|---|
| Total weight (g) | 604 ± 52.8 | 630 ± 71.4 | 638 ± 59.6* |
| Hull weight (g) | 260 ± 28.3 | 283 ± 35.0* | 284 ± 24.4* |
| Non-sieved brown rice weight (g) | 208 ± 24.2 | 227 ± 28.9* | 228 ± 20.1* |
| Sieved brown rice (g) | 201 ± 24.6 | 218 ± 29.0* | 221 ± 19.5* |
| Increasing rate (%) | | 8.9 | 10.2 |
| Thousand kernel weight (g) | 23.6 ± 0.5 | 23.0 ± 0.5* | 23.5 ± 0.3 |

| Per 10 plants | 0.5 mM AOH Basal fertilizer | 0.5 mM AOH Topdressing at panicle formation |
|---|---|---|
| Total weight (g) | 644 ± 49.5* | 643 ± 54.1* |
| Hull weight (g) | 288 ± 23.9* | 279 ± 24.9* |
| Non-sieved brown rice weight (g) | 230 ± 19.7* | 224 ± 20.9* |
| Sieved brown rice (g) | 222 ± 19.8* | 215 ± 20.7* |
| Increasing rate (%) | 10.5 | 7.2 |
| Thousand kernel weight (g) | 23.5 ± 0.6 | 23.4 ± 0.5 |

Example 11

Production of 3-Methyl-AOH

According to the following method, 3-methyl-AOH was produced from AOH.

To 5 mL of DMSO (anhydrous dimethyl sulfoxide), 153 mg of AOH was dissolved at 50° C., 0.075 mL of iodomethane was added thereto, and the resultant mixture was reacted for 4 hours. A fraction obtained using preparative thin-layer chromatography (TLC, mobile phase $CH_2Cl_2$:methanol=9:1) was further subjected to HPLC (Develosil C30-UG-5 column (size 20×250 mm, flow rate: 5 mL/minute, mobile phase: 10% methanol in 0.05% trifluoroacetic acid, detection: UV 310 nm) to yield 10.2 mg (yield 6.11%) of 3-methyl-AOH.

It was confirmed by the measurement results of mass spectrometry, $^1$H-NMR and $^{13}$C-NMR that the produced substance was 3-methyl-AOH, and the details were as follows.

When the sample was measured with a mass spectrometer (JMS-T100LC mass spectrometer) in the positive mode, m/z 168$[M+H]^+$ and m/z 190$[M+Na]^+$ were indicated.

Additionally, with $^1$H-NMR and $^{13}$C-NMR, the sample showed the following values.

$^1$H-NMR (500 MHz) δ 3.88

$^{13}$C-NMR (125 MHz) δ 37.9, 112.8, 142.1, 148.0, 152.7

Example 12

The Influence of AOH and 3-Methyl-AOH on Rice

Figure 8:
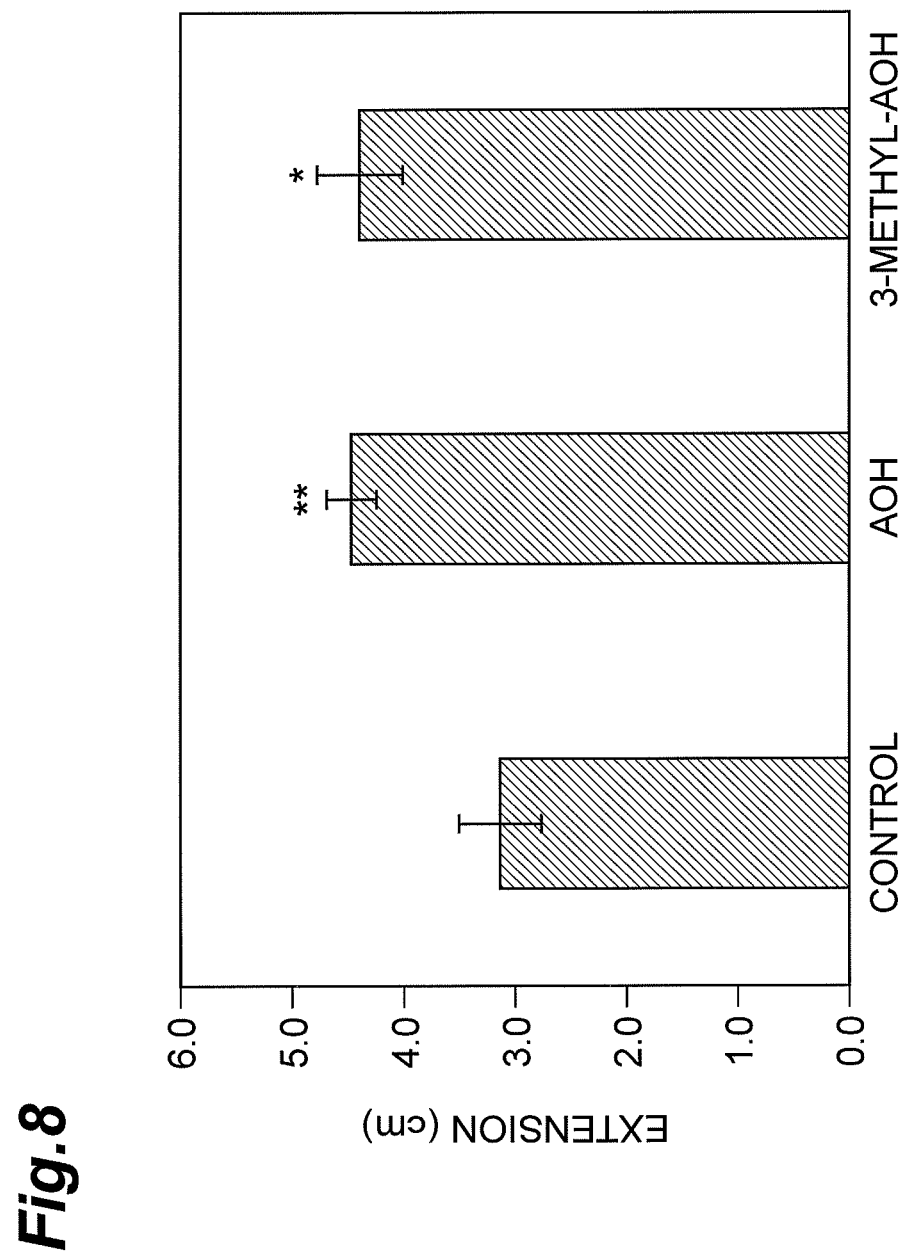
FIG. 8 is a graph showing the influence of addition of AOH or 3-methyl-AOH to a medium on rice growth.

Sterilized seeds of rice (Nipponbare) (*Oryza sativa* L. cv. Nipponbare) were allowed to sprout at 28° C. in three days. The sprouted seeds (four seeds per test tube) were cultivated in a test tube, in which a control culture fluid, a culture fluid to which 0.2 mM of AOH was added, or a culture fluid to which 0.2 mM of 3-methyl-AOH was added and was placed, at 28° C. for a week. The control culture fluid comprises 0.5 mM of $NH_4NO_3$, 0.3 mM of $Na_2HPO_4$, 0.15 mM of $K_2SO_4$, 0.2 mM of $MgCl_2$, 0.1 mM of $CaCl_2$, 23 µM of Fe-ethylenediaminetetraacetic acid (Fe-EDTA), 25 µM of $H_3BO_3$, 4.5 µM of $MnSO_4$, 0.15 µM of $CuSO_4$, 0.35 µM of $ZnSO_4$, and 0.05 µM of $Na_2MoO_4$. The culture fluid was replaced with new culture fluid every other day. After cultivation, the length of shoots and roots was measured. The measured extension of the roots is shown in FIG. 8. It was confirmed that 3-methyl-AOH, similarly to AOH, had extension activity for roots. (In FIG. 8, "*" indicates P value <0.05, and "**" indicates P value <0.01. n=16.). In contrast, 3-methyl-AOH gave no influence on extension of the shoots.

INDUSTRIAL APPLICABILITY

Since having a growth regulating action, AOH and 3-methyl-AOH of the present invention can be effectively used as plant growth regulators. Such plant growth regulators can be widely applied to agriculture and gardening.

The invention claimed is:

1. A compound selected from the group consisting of the following (A) and (B):

(A) 3H-imidazo[4,5-d][1,2,3]triazin-4,6(5H,7H)-dione; and (B) 3-methyl-3H-imidazo[4,5-d][1,2,3]triazin-4,6(5H,7H)-dione.

2. A plant growth regulator comprising the compound according to claim 1.

3. A method for producing 3H-imidazo[4,5-d][1,2,3]triazin-4,6(5H,7H)-dione, comprising:

allowing xanthine oxidase to act on 7H-imidazo[4,5-d][1,2,3]triazin-4(3H)-one to yield 3H-imidazo[4,5-d][1,2,3]triazin-4,6(5H,7H)-dione.

4. A method for producing 3H-imidazo[4,5-d][1,2,3]triazin-4,6(5H,7H)-dione comprising steps of:

extracting a plant body to prepare an extract; and isolating 3H-imidazo[4,5-d][1,2,3]triazin-4,6(5H,7H)-dione from the extract.

* * * * *